United States Patent
Guillon et al.

(10) Patent No.: US 7,982,083 B2
(45) Date of Patent: Jul. 19, 2011

(54) CATALYST COMPRISING AN EUO ZEOLITE, A 10 MR ZEOLITE AND A 12 MR ZEOLITE, AND ITS USE IN ISOMERIZING AROMATIC C8 COMPOUNDS

(75) Inventors: Emmanuelle Guillon, Vernaison (FR); Eric Sanchez, Saint Genis Laval (FR); Sylvie Lacombe, Vernaison (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 236 days.

(21) Appl. No.: 12/158,753

(22) PCT Filed: Dec. 1, 2006

(86) PCT No.: PCT/FR2006/002647
§ 371 (c)(1),
(2), (4) Date: Nov. 5, 2008

(87) PCT Pub. No.: WO2007/080246
PCT Pub. Date: Jul. 19, 2007

(65) Prior Publication Data
US 2009/0093661 A1 Apr. 9, 2009

(30) Foreign Application Priority Data
Dec. 22, 2005 (FR) ...................... 05 13176

(51) Int. Cl.
*C07C 5/22* (2006.01)
*B01J 29/06* (2006.01)

(52) U.S. Cl. ........ 585/477; 585/480; 585/481; 585/482; 502/60; 502/63; 502/64; 502/66; 502/67; 502/68; 502/71; 502/74; 502/77; 502/78

(58) Field of Classification Search ............ 502/60, 502/63, 64, 66, 67, 68, 71, 74, 77, 78
See application file for complete search history.

(56) References Cited

U.S. PATENT DOCUMENTS

| 4,537,754 A | 8/1985 | Casci et al. |
| 5,759,950 A | 6/1998 | Cheng et al. |
| 5,800,698 A | 9/1998 | Torrealba et al. |
| 6,008,425 A * | 12/1999 | Mohr et al. ............ 585/481 |
| 6,057,486 A * | 5/2000 | Merlen et al. .......... 585/481 |
| 6,344,135 B1 | 2/2002 | Benazzi et al. |
| 6,576,581 B1 * | 6/2003 | Sharma et al. ......... 502/66 |
| 6,613,709 B1 | 9/2003 | Merlen et al. |
| 6,872,866 B1 | 3/2005 | Nemeth et al. |
| 7,419,931 B2 | 9/2008 | Serra et al. |
| 2004/0087823 A1 * | 5/2004 | McMinn et al. ....... 585/481 |
| 2005/0202955 A1 * | 9/2005 | McMinn et al. ....... 502/64 |
| 2005/0234279 A1 | 10/2005 | Serra et al. |

FOREIGN PATENT DOCUMENTS

| EP | 0923987 | 6/1999 |
| EP | 1077083 A | 2/2001 |
| EP | 1586376 A1 | 10/2005 |
| FR | 2790001 A | 8/2000 |
| WO | WO 99/28031 | 6/1999 |
| WO | WO 00/38834 A | 7/2000 |
| WO | WO 00/66263 | 11/2000 |
| WO | WO 2004/016278 A1 | 6/2004 |

OTHER PUBLICATIONS

International Search Report and Written Opinion conducted Jun. 14, 2007 for International Patent Application No. PCT/FR2006/002647 filed Dec. 1, 2006.

Moreau, F. et al., "Ethylbenzene isomerization over bifuntional platinum alumina-EUO catalysts: Location of the active sites," Microporous and Mesoporous Materials, 2006, vol. 90, No. 1-3, pp. 327-338.

* cited by examiner

*Primary Examiner* — Elizabeth D Wood
(74) *Attorney, Agent, or Firm* — Millen, White, Zelano & Branigan, P.C.

(57) ABSTRACT

A catalyst is described which comprises at least one zeolite with structure type EUO, at least one zeolite having channels the opening to which is defined by a ring of 10 oxygen atoms (10 MR), at least one zeolite having channels the opening to which is defined by a ring of 12 oxygen atoms (12 MR) and at least one porous mineral matrix. Said catalyst optionally also contains at least one group VIII metal. The catalyst of the invention is used in a process for isomerizing a feed comprising aromatic compounds containing 8 carbon atoms per molecule.

27 Claims, No Drawings

CATALYST COMPRISING AN EUO ZEOLITE, A 10 MR ZEOLITE AND A 12 MR ZEOLITE, AND ITS USE IN ISOMERIZING AROMATIC C8 COMPOUNDS

TECHNICAL FIELD

The present invention relates to a catalyst formed from at least three distinct zeolites for use, for example, in aromatic hydrocarbon transformation reactions. More precisely, it concerns a catalyst for isomerizing C8 aromatic compounds. The present invention also relates to the use of said catalyst in a process for isomerizing a feed comprising aromatic compounds containing eight carbon atoms per molecule.

PRIOR ART

In known processes for isomerizing aromatic compounds containing eight carbon atoms (AC8), a feed which is generally low in para-xylene with respect to the thermodynamic equilibrium of the mixture (i.e. with a much lower para-xylene content than that of a mixture at thermodynamic equilibrium at the temperature under consideration, that mixture comprising at least one compound selected from the group formed by meta-xylene, ortho-xylene, para-xylene and ethylbenzene) and generally rich in ethylbenzene compared with that same mixture at thermodynamic equilibrium, is introduced into a reactor containing at least one catalyst, under suitable temperature and pressure conditions to obtain at the reactor outlet a composition of aromatic compounds containing eight carbon atoms which is as close as possible to the composition of said mixture at thermodynamic equilibrium at the temperature of the reactor. To obtain such a composition, the skilled person is generally constrained to maximise the conversion of ethylbenzene present in the feed. From the mixture obtained at the outlet from the isomerization reactor, xylene is separated, possibly along with meta-xylene or ortho-xylene which are the desired isomers as they are of great importance, in particular for the synthetic fibre industry.

The catalysts used to carry out a process for isomerizing aromatic compounds containing eight carbon atoms are generally zeolitic catalysts. Prior art catalysts, in particular catalysts based on mordenite zeolite, only produce mediocre catalytic performances as non-negligible side reactions occurring in their presence generate losses. An example which may be cited of such secondary reactions is naphthene ring opening, which may or may not be followed by cracking (losses to paraffins) or disproportionation and transalkylation reactions of aromatics containing eight carbon atoms (losses to unwanted aromatic compounds), or hydrogenation of aromatic compounds (losses to naphthenes). Catalysts based on ZSM-5 zeolite, alone or mixed with other zeolites such as mordenite, for example, have already been used but also do not produce optimum catalytic performances. More recently, a catalyst has been proposed which is based on a zeolite with structure type EUO (EP-A1-0 923 987). The present invention thus proposes to provide a novel catalyst with a composition such that when it is used to isomerize aromatic compounds containing eight carbon atoms per molecule, the ethylbenzene conversion is improved and secondary reactions are limited, thereby reducing losses.

SUMMARY OF THE INVENTION

The present invention provides a catalyst comprising at least one zeolite with structure type EUO, at least one zeolite having channels the opening to which is defined by a ring of 10 oxygen atoms (10 MR), at least one zeolite having channels the opening to which is defined by a ring of 12 oxygen atoms (12 MR) and at least one porous mineral matrix. Advantageously, the catalyst of the invention comprises at least one metal selected from metals from groups VIB, VIIB and VIII of the periodic table of the elements, and optionally also at least one metal selected from metals from groups IIIA and IVA of the periodic table of the elements. Each of the zeolites included in the catalyst of the invention contains silicon and at least one element T selected from the group formed by aluminium, iron, gallium and boron, preferably aluminium.

The present invention also concerns the use of said catalyst in a process for isomerizing a feed comprising aromatic compounds containing eight carbon atoms per molecule.

ADVANTAGE OF THE INVENTION

It has surprisingly been discovered that a composite catalyst comprising a combination of at least one zeolite with structure type EUO, at least one zeolite having channels the opening to which is defined by a ring of 10 oxygen atoms (10 MR), and at least one zeolite having channels the opening to which is defined by a ring of 12 oxygen atoms (12 MR) results in improved catalytic performances in reactions for isomerizing aromatic compounds containing eight carbon atoms per molecule. In particular, the catalyst of the invention leads to an ethylbenzene conversion which is higher than that achieved by prior art catalysts, in particular catalysts based on a zeolite with structure type EUO or structure type MOR. Further, the catalyst of the invention limits secondary reactions substantially, thereby generating fewer losses, compared with prior art catalysts.

Further, by adjusting the relative quantity of the three zeolites, namely that with structure type EUO, that with 10 MR and that with 12 MR, in the catalyst of the invention, it is possible to process a very wide range of mixtures of hydrocarbon feeds.

DESCRIPTION

The present invention provides a catalyst comprising at least one zeolite with structure type EUO, at least one zeolite having channels the opening to which is defined by a ring of 10 oxygen atoms (10 MR), at least one zeolite having channels the opening to which is defined by a ring of 12 oxygen atoms (12 MR) and at least one porous mineral matrix.

In accordance with the invention, the catalyst comprises at least three zeolites with different structure types.

The zeolite with structure type EUO present in the catalyst of the invention has already been described in the art. It has a uni-dimensional microporous network with a pore diameter of 4.1×5.4 Å (1 Å=1 Angstrom=$10^{-10}$ m) ("Atlas of zeolite framework types", W M Meier, D H Olson and Ch Baerlocher, $5^{th}$ Edition, 2001). Further, N A Briscoe et al have disclosed, in an article in the review "Zeolites" (1988, 8, 74) that these uni-dimensional channels have side pockets with a depth of 8.1 Å and a diameter of 6.8×5.8 Å. The zeolite with structure type EUO includes the zeolites EU-1 (EP-B1-0 042 226), ZSM-50 (U.S. Pat. No. 4,640,829) and TPZ-3 (EP-A1-0 051 318). The zeolite with structure type EUO present in the catalyst of the invention is preferably an EU-1 zeolite.

Zeolites having channels the opening to which is defined by a ring of 10 oxygen atoms and those with channels the opening to which is defined by a ring of 12 oxygen atoms are defined in the "Atlas of zeolite framework types", W M Meier, D H Olson and Ch Baerlocher, $5^{th}$ Edition, 2001, Elsevier, which is also referred to in the present application. The zeolites therein are classified according to the size of their pore openings or channels. In accordance with the invention, at least one zeolite included in the catalyst of the invention has pores or channels the opening to which is defined by a ring of 10 oxygen atoms (10 MR opening) and at least one other zeolite in the catalyst of the invention has pores or channels the opening to which is defined by a ring of 12 oxygen atoms (12 MR opening). In accordance with the invention, the channels of the zeolite with a 10 MR opening, hereinafter denoted 10 MR zeolite, are the principal channels which open directly to the exterior of said zeolite. The 10 MR zeolite may also comprise internal secondary channels, for example 12 MR channels, which are accessible uniquely via the principal 10 MR channels. The zeolite with a 12 MR opening, hereinafter termed the 12 MR zeolite, has at least principal 12 MR channels opening directly to the exterior of said zeolite.

The zeolite with structure type EUO, and the 10 MR zeolite and 12 MR zeolites present in the catalyst of the invention comprise silicon and at least one element T selected from the group formed by aluminium, iron, gallium and boron, preferably aluminium. They are preferably practically entirely in the acid form.

The zeolite with structure type EUO, present in the catalyst of the invention, is preferably an EU-1 zeolite. It is characterized by a Si/T atomic ratio, preferably an Si/Al atomic ratio, of at least 5, advantageously in the range 5 to 100. Said zeolite with structure type EUO is at least partially, preferably practically completely in the acid form, i.e. in the hydrogen form $H^+$, the sodium content preferably being such that the atomic ratio Na/T is less than 0.1, preferably less than 0.05 and more preferably less than 0.01. A mode for synthesizing an EU-1 zeolite is described in EP-B1-0 042 226. A mode for synthesizing a ZSM-50 zeolite is described in U.S. Pat. No. 4,640,829. A mode for synthesizing a TPZ-3 zeolite is described in EP-A1 0 051 318.

The 10 MR zeolite present in the catalyst of the invention is characterized by a Si/T atomic ratio, preferably a Si/Al atomic ratio, in the range 2 to 250, preferably in the range 5 to 150 and more preferably in the range 10 to 80. The sodium content is less than 0.2% by weight, preferably less than 0.1% by weight and more preferably less than 0.05% by weight with respect to the total weight of dry zeolite. Any zeolite with channels the opening to which is defined by a ring with 10 oxygen atoms (10 MR) and known in the prior art is suitable for producing the catalyst of the present invention. The 10 MR zeolite is advantageously selected from zeolites with structure type MFI, TON, NES an FER. Highly preferably, the 10 MR zeolite is selected from ZSM-5, NU-87, IM-5, ferrierite, NU-85 and ZSM-22 zeolites. Highly advantageously, it is ZSM-5 zeolite. These zeolites and their mode of preparation are well known to the skilled person; NU-85 zeolite is described in particular in U.S. Pat. No. 5,446,234; IM-5 zeolite is particularly described in EP-A-0 946 416 and U.S. Pat. No. 6,136,290.

The 12 MR zeolite present in the catalyst of the invention is characterized by a Si/T atomic ratio, preferably a Si/Al atomic ratio, in the range 2 to 250, preferably in the range 5 to 150 and highly preferably in the range 10 to 80. The sodium content is less than 0.2% by weight, preferably less than 0.1% by weight and highly preferably less than 0.05% by weight with respect to the total weight of dry zeolite. Any zeolite with channels (principal or secondary) the opening to which is defined by a ring with 12 oxygen atoms (12 MR) and known in the prior art are suitable for producing the catalyst of the present invention. The 12 MR zeolite is advantageously selected from zeolites with structure type BEA, MOR, MAZ, FAU, MTW and BOG. Highly preferably, the 12 MR zeolite is selected from beta, Y, mordenite, ZSM-12, mazzite and boggsite zeolites. Boggsite has principal channels with 10 MR and 12 MR. More preferably, the 12 MR present in the catalyst of the invention is mordenite or beta zeolite.

The catalyst of the invention optionally comprises at least one zeolite with channels the opening to which is defined by a ring of 8 oxygen atoms. According to the invention, the channels of the zeolite with an 8 MR opening, hereinafter termed 8 MR zeolite, are principal channels which open directly to the exterior of said zeolite and which do not have channels with larger pore openings. Said 8 MR zeolite which is advantageously present in the catalyst of the invention comprises silicon and at least one element T selected from the group formed by aluminium, iron, gallium and boron, preferably aluminium. It is preferably practically entirely in the acid form. Said 8 MR zeolite is characterized by a Si/T atomic ratio, preferably a Si/Al atomic ratio, in the range 2 to 250, preferably in the range 5 to 150 and more preferably in the range 10 to 80. The sodium content is less than 0.2% by weight, preferably less than 0.1% by weight and more preferably less than 0.05% by weight with respect to the total weight of dry zeolite. Any zeolite with channels the opening to which is defined by a ring with 8 oxygen atoms (8 MR) and known in the prior art is suitable for producing the catalyst of the present invention. The 8 MR zeolite is advantageously selected from zeolites with structure type ERI, ESV and LTA. Preferably, the preferred 8 MR zeolites are selected from erionite, ERS-7 and Linde type A zeolites. These zeolites and their mode of preparation are well known to the skilled person.

The crystals of the zeolite with structure type EUO, those of the 10 MR zeolite, those of the 12 MR zeolite and those of the optional 8 MR zeolite are clearly distinguished from each other; there is no confusion.

The atomic ratio Si/T, preferably the atomic ratio Si/Al, of the zeolites described above are those obtained after synthesis of said zeolites, or those obtained after post-synthesis extraction of a portion of the T atoms, termed dealumination treatments when the element T is aluminium, which are well known to the skilled person; non-exhaustive examples are hydrothermal treatments which may or may not be followed by acid attacks or direct acid attacks using solutions of mineral or organic acids to extract a portion of the T atoms, preferably a portion of the aluminium atoms, from the zeolitic framework.

The atomic ratio Si/T, preferably the atomic ratio Si/Al, of the zeolite with structure type EUO, the 10 MR and 12 MR zeolites and optional 8 MR zeolite forming part of the composition of the catalyst of the invention and the chemical composition of said catalyst are determined by X ray fluorescence and atomic absorption.

The zeolite with structure type EUO, 10 MR and 12 MR zeolites and optional 8 MR zeolite forming part of the composition of the catalyst of the invention may be calcined and exchanged by at least one treatment using a solution of at least one ammonium salt to obtain the ammonium form of the zeolites which, once calcined, produce the hydrogen form of said zeolites.

The zeolite with structure type EUO, 10 MR and 12 MR zeolites and optional 8 MR zeolite forming part of the composition of the catalyst of the invention are at least partially, preferably practically entirely in the acid form, i.e. in the hydrogen form ($H^+$). The atomic ratio Na/T is generally less than 10%, preferably less than 5% and still more preferably less than 1%.

The 10 MR and 12 MR zeolites and optional 8 MR zeolite are catalogued in the Atlas of zeolites and are synthesised using the methods described in that work ("Atlas of zeolite framework types", W M Meier, D H Olson and Ch Baerlocher, 5$^{th}$ Edition, 2001) or any other method described in the literature accessible to the skilled person. Any commercially available zeolite may be used to obtain the catalyst of the invention.

The porous mineral matrix present in the catalyst of the invention is generally selected from elements from the group formed by clays (for example natural clays such as kaolin, sepiolite, attapulgite or bentonite), magnesia, aluminas, silicas, titanium oxide, boron oxide, zirconia, aluminium phosphates, titanium phosphates, zirconium phosphates, amorphous silica-aluminas and coal, preferably from elements of the group formed by aluminas, clays, mixtures of alumina and silica and mixtures of alumina and silica-alumina, and more preferably from aluminas and in particular gamma alumina.

Advantageously, the catalyst of the invention comprises at least one metal selected from metals from groups VIB, VIIB and VIII of the periodic table of the elements, highly advantageously from metals from groups VIIB and VIII and more advantageously from metals from group VIII of the periodic table of the elements. Preferably, the group VIB metal is molybdenum. Preferably, the group VIIB metal is rhenium. Preferably, the group VIII metal is selected from platinum and palladium, more preferably platinum. The weight content of said element is preferably in the range 0.01% to 5% by weight, preferably in the range 0.01% to 2% by weight and more preferably in the range 0.05% to 1% by weight with respect to the total weight of said catalyst.

According to the invention, the catalytic composition of the catalyst advantageously contains at least one metal from group VIII of the periodic table of the elements, preferably selected from the group formed by platinum and palladium; more preferably, said group VIII metal is platinum. The weight content of said group VIII metal is generally in the range 0.01% to 2.0% by weight, preferably in the range 0.05% to 1.0% by weight with respect to the total catalyst weight. Preferably, the dispersion in the catalyst of the group VIII metal, preferably platinum, determined by chemisorption, for example by $H_2$—$O_2$ titration or by chemisorption of carbon monoxide, is more than 50%, highly preferably more than 70%.

Highly advantageously, said catalytic composition of the catalyst of the invention contains, in addition to at least one metal selected from metals from groups VIB, VIIB and VIII, at least one metal selected from metals from groups IIIA and IVA. Said metal selected from metals from groups IIIA and IVA is present in an amount in the range 0.01% to 5.0% by weight, preferably in the range 0.05% to 1.0% by weight with respect to the total catalyst weight. Preferably, the group IIIA metal is indium. Preferably, the group IVA metal is tin.

The catalyst of the invention, preferably formed into beads or extrudates and more preferably into the form of extrudates, contains, with respect to the weight of the catalyst:
  1% to 90%, preferably 3% to 60% and more preferably 3% to 40% of at least one zeolite with structure type EUO, at least one zeolite with channels the opening to which is defined by a ring of 10 oxygen atoms (10 MR) and at least one zeolite with channels the opening to which is defined by a ring of 12 oxygen atoms (12 MR), and optionally at least one zeolite with channels the opening to which is defined by a ring of 8 oxygen atoms (8 MR);
  0 to 5.0%, preferably 0.01% to 5.0%, more preferably 0.01% to 2.0% and still more preferably 0.05% to 1.0% of at least one hydrodehydrogenating metal selected from metals from groups VIB, VIIB and VIII;
  optionally, at least one additional metal selected from metals from group IIIA and IVA, the content by weight being in the range 0.01% to 5.0%, preferably in the range 0.05% to 1.0%;
  optionally, sulphur;
  at least one porous mineral matrix, termed a binder, providing the complement to 100% in the catalyst. The porous mineral matrix is generally selected from elements from the group formed by clays (for example from natural clays such as kaolin, sepiolite, attapulgite or bentonite), magnesia, aluminas, silicas, titanium oxide, boron oxide, zirconia, aluminium phosphates, titanium phosphates, zirconium phosphates, amorphous silica aluminas and coal, preferably of elements from the group formed by aluminas, clays, mixtures of alumina and silica and mixtures of alumina and silica alumina, more preferably from aluminas and in particular gamma alumina.

In general, and in a first implementation of the process for preparing a catalyst of the invention, the catalyst is prepared by mixing at least one zeolite with structure type EUO, at least one 10 MR zeolite and at least one 12 MR zeolite, and at least one optional 8 MR zeolite, said zeolites being in the powder state. The mixture of said zeolites is produced using any powder mixing technique known to the skilled person. Once the mixture of zeolite powders has been produced, the mixture is formed using any technique which is known to the skilled person. In particular, it may be mixed with a porous mineral matrix, generally amorphous, for example with a moist alumina gel powder. The mixture is then formed, for example by extrusion through a die. Forming may be carried out with matrices other than alumina, such as magnesia, amorphous silica-aluminas, natural clays (kaolin, bentonite, sepiolite, attapulgite), silica, titanium oxide, boron oxide, zirconia, aluminium phosphates, titanium phosphates, zirconium phosphates, coal and mixtures thereof. Preferably, matrices containing alumina are used, in any of the forms known to the skilled person, and more preferably gamma alumina. It may also be advantageous to use mixtures of alumina and silica, or mixtures of alumina and silica-alumina. Techniques other than extrusion, such as pelletization or bowl granulation, may be employed. After the forming step, the catalyst obtained undergoes a drying step carried out at a temperature in the range 80° C. to 150° C. then a calcining step carried out at a temperature in the range 300° C. to 600° C., preferably in the range 400° C. to 550° C.

In the case in which the catalyst of the invention comprises at least one metal selected from metals from groups VIB, VIIB and VIII of the periodic table of the elements, said metal(s) is (are) deposited on a catalytic support after forming the zeolites which are free of metals, using any process which is known to the skilled person and which can allow a metal to be deposited onto the catalytic support. The term "catalytic support" means a mixture of zeolites (free of metals) with at least one porous mineral matrix after forming, drying and calcining as described above. Said catalytic support of the catalyst of the present invention generally has the following quantities of matrix and zeolites:
  1% to 90% by weight, preferably 3% to 60% by weight, more preferably 3% to 40% by weight of zeolites such that at least one zeolite is a zeolite with structure type EUO, at least one zeolite is a zeolite selected from 10 MR zeolites, at least one zeolite is selected from 12 MR zeolites and optionally at least one zeolite is selected from 8 MR zeolites;

10% to 99% by weight, preferably 40% to 97% by weight, more preferably 60% to 97% by weight of at least one amorphous or low crystallinity oxide type porous mineral matrix.

A second implementation of the process for preparing a catalyst of the invention, in the preferred case in which said catalyst comprises at least one metal selected from metals from groups VIB, VIIB and VIII of the periodic table of the elements, consists of subjecting at least one of the zeolites described above and comprised in said catalyst to deposition of at least one metal selected from metals from groups VIB, VIIB and VIII, prior to forming the zeolite ensemble.

Preferably, at least one EU-1 zeolite is subjected to deposition of at least one metal selected from metals from groups VIB, VIIB and VIII. It is also advantageous to deposit on the 10 MR zeolite at least one metal selected from metals from groups VIB, VIIB and VIII and to deposit on the 12 MR zeolite at least one other metal selected from metals from groups VIB, VIIB and VIII. It is also advantageous, in the second implementation of the process for preparing the catalyst of the invention, to deposit, on each of the zeolites present in the catalyst of the invention, the same metal selected from metals from groups VIB, VIIB and VIII, preferably to deposit at least one metal from group VIII and more preferably to deposit platinum. The mixture of these zeolites, which are then in the powder state, at least one of the zeolites being charged with metal(s), is produced using any powder mixing technique which is known to the skilled person. Once the mixture of zeolite powders has been formed, wherein at least one of the powders is charged with metal(s), the mixture is formed using any technique which is known to the skilled person. In particular, it may be mixed with a porous mineral matrix, generally amorphous, for example a moist alumina gel powder. The mixture is then formed, for example by extrusion through a die. Forming may be carried out with matrices other than alumina, such as magnesia, amorphous silica-aluminas, natural clays (kaolin, bentonite, sepiolite, attapulgite), silica, titanium oxide, boron oxide, zirconia, aluminium phosphates, titanium phosphates, zirconium phosphates, coal and mixtures thereof, for example. Preferably, matrices containing alumina are used, in any of the forms known to the skilled person, and more preferably gamma alumina. It may also be advantageous to use mixtures of alumina and silica, or mixtures of alumina and silica-alumina. Techniques other than extrusion, such as pelletization or bowl granulation, may be used. After the forming step, the product obtained undergoes a drying step carried out at a temperature in the range 80° C. to 150° C. then a calcining step carried out at a temperature in the range 300° C. to 600° C., preferably in the range 400° C. to 550° C.

To deposit the metal on at least one zeolite as described above and/or onto the catalytic support in accordance with the first or the second implementation of the process for preparing the catalyst of the invention, it is possible to use a technique for cationic exchange with competition, wherein the competitor is preferably ammonium nitrate, the competition ratio between the competitor and the metallic precursor being at least about 5 and advantageously in the range 5 to 200. The dry impregnation or co-precipitation technique may also be used.

The sources of group VIII metals which may be used are well known to the skilled person. Examples which may be used are nitrates, sulphates, phosphates, halides, for example chlorides, bromides or fluorides, carboxylates, for example acetates, and carbonates. In the case of platinum, hexachloroplatinic acid or platinum tetramine is preferably used. Sources of group VIIB metals which may be used are also well known to the skilled person. In the case of rhenium, an ammonium perrhenate complex $(NH_4)ReO_4$ or perrhenic acid is usually used. Sources of metals from group VIB which may be used are also well known to the skilled person. In the case of molybdenum, it is possible to use molybdic acids and their salts, in particular their ammonium salts such as ammonium molybdate, ammonium heptamolybdate as well as phosphomolybdic acid. Preferably, ammonium heptamolybdate $(NH_4)_6Mo_7O_{24}$ is used. Deposition of the metal(s) is generally followed by calcining in air or oxygen, usually between 300° C. and 600° C. for 0.5 to 10 hours, preferably between 350° C. and 550° C. for 1 to 4 hours. Next, reduction in hydrogen may be carried out, generally at a temperature in the range 300° C. to 600° C. for 1 to 10 hours, preferably between 350° C. and 550° C. for 2 to 5 hours.

In the first or said second implementation for preparing the catalyst of the invention, and in the preferred case in which said catalyst comprises at least one metal selected from metals from groups VIB, VIIB and VIII of the periodic table of the elements and at least one optional additional metal selected from metals from groups IIIA and IVA, the metals may also be deposited not directly on the zeolites but on the porous mineral matrix (for example the alumina binder) of the catalytic support formed by the three zeolites, optionally the four zeolites, and at least one matrix, before or after the forming step, using anionic exchange. An example which may be cited in the case of deposition of platinum is the use of the hexachloroplatinic complex $H_2PtCl_6$ and in the case of deposition of rhenium, the use of perrhenic acid $HReO_4$. In general, after depositing the metal(s), as before, the catalyst undergoes calcining then reduction in hydrogen as indicated above.

When the catalyst of the invention contains several metals, they may be introduced either in the same manner or using different techniques, before or after forming depending on the catalyst preparation mode employed, and in any order. In the case in which the technique used is ion exchange, several exchanges in succession may be necessary to introduce the required quantities of metals.

Regardless of the mode for preparing the catalyst of the invention, after calcining said catalyst, reduction may be carried out in hydrogen, generally at a temperature in the range 300° C. to 600° C., preferably in the range 350° C. to 550° C., for a period in the range 1 to 10 hours, preferably 2 to 5 hours. Such a reduction may be carried out ex situ or in situ, with respect to the place of use of said catalyst in a given reaction.

The distribution between the three zeolites, optionally the four zeolites, of each of the groups defined above is such that the amount of each of the zeolites present in the catalyst of the invention can be between 1% and 98% by weight, preferably 2% to 60% by weight and more preferably 4% to 50% by weight, as a percentage by weight of a zeolite with respect to the ensemble of the zeolites introduced into the catalyst.

The catalyst of the present invention is formed into grains with different shapes and dimensions. It is generally used in the form of cylindrical extrudates or polylobed extrudates such as bilobes, trilobes, or polylobes with a straight or twisted shape, but may optionally be manufactured and used in the form of powder, pellets, tablets, rings, beads or wheels.

The catalyst of the present invention may optionally contain sulphur. In this case, the sulphur is introduced into the formed and calcined catalyst containing the element(s) cited above, either in situ before the catalytic reaction or ex situ. Sulphurization is carried out using any sulphurizing agent which is known to the skilled person, such as dimethyldisulphide or hydrogen sulphide. Any sulphurization is carried out after reduction. In the case of in situ sulphurization, if the catalyst has not already been reduced, reduction is carried out before sulphurization. In the case of ex situ sulphurization, reduction is carried out followed by sulphurization.

The invention also concerns the use of the catalyst of the invention in processes for converting hydrocarbons. More precisely, the present invention concerns a process for isomerizing a feed comprising aromatic compounds containing eight carbon atoms per molecule carried out in the presence of a catalyst in accordance with the invention. Said feed comprises a mixture of xylenes and ethylbenzene. Said process is carried out in the gas phase, preferably in the absence of any liquid phase. Said process is generally carried out under the following operating conditions:

a temperature in the range 300° C. to 500° C., preferably in the range 320° C. to 450° C. and more preferably in the range 340° C. to 430° C.;

a partial pressure of hydrogen in the range 0.3 to 1.5 MPa, preferably in the range 0.4 to 1.2 MPa and more preferably in the range 0.7 to 1.2 MPa;

a total pressure in the range 0.45 to 1.9 MPa, preferably in the range 0.6 to 1.5 MPa;

an hourly space velocity, expressed in kilograms of feed introduced per kilogram of catalyst per hour, in the range 0.25 to 30 $h^{-1}$, preferably in the range 1 to 10 $h^{-1}$, and more preferably in the range 2 to 6 $h^{-1}$.

The following examples illustrate the invention without in any way limiting its scope.

EXAMPLE 1

Preparation of a Catalyst Based on a Zeolite with Structure Type EUO (Comparative)

The starting material used was an as synthesised EU-1 zeolite comprising an organic template, silicon and aluminium, with an overall Si/Al atomic ratio of 13.6, a sodium weight content with respect to the weight of dry EU-1 zeolite of about 1.5%, corresponding to a Na/Al atomic ratio of 0.6. This EU-1 zeolite initially underwent dry calcining at 550° C. in a stream of air for 6 hours. Next, the solid obtained underwent three ion exchanges in a 10N $NH_4NO_3$ solution at about 100° C. for 4 hours for each exchange. At the end of these treatments, the EU-1 zeolite in the $NH_4NO_3$ form had an overall Si/Al atomic ratio of 18.3, and a sodium weight content with respect to the weight of dry EU-1 zeolite of 50 ppm, corresponding to a Na/Al atomic ratio of 0.003. The EU-1 zeolite was then formed by extrusion with an alumina gel to obtain, after drying and calcining in dry air, the support constituted by extrudates 1.4 mm in diameter, which contained 15% by weight of EU-1 zeolite in the H form and 85% of alumina.

The support obtained underwent anionic exchange with hexachloroplatinic acid in the presence of a competing agent (hydrochloric acid), to introduce 0.3% by weight of platinum with respect to the weight of catalyst. The moist solid was then dried at 120° C. for 12 hours and calcined in a flow of dry air at a temperature of 500° C. for one hour. The catalyst C0 thus obtained contained 15.0% by weight of EU-1 zeolite in the H form, 84.7% by weight of alumina and 0.3% by weight of platinum.

EXAMPLE 2

Preparation of Catalysts Based on Zeolite With Structure Type EUO, a 10 MR Zeolite and a 12 MR Zeolite (in Accordance with the Invention)

The zeolites used to prepare the catalysts illustrating the invention are shown in Table 1 with their composition (Si/Al atomic ratio) and their residual sodium content. The zeolites concerned are in the acid form.

The EU-1 zeolite was synthesized in the manner described in Example 1. After calcining in air at 550° C. then after 3 ion exchanges in a 10N $NH_4NO_3$ solution for 4 h, it had a Si/Al atomic ratio of 18.3 and a Na/Al atomic ratio of 0.003, corresponding to a Na content of 50 ppm.

The beta, mordenite, Y and ZSM-5 zeolites were commercially available zeolites (Zeolyst).

The NU-87 zeolite was synthesized in accordance with European patent application EP-A-0 377 291 or EP-B-0 378 916. It had an overall Si/Al atomic ratio of 17.2 and a sodium content of 1256 ppm by weight. This NU-87 zeolite initially underwent dry calcining at 550° C. in a stream of air and nitrogen for 6 hours. Next, the solid obtained underwent ion exchange in a 10N $NH_4NO_3$ solution at about 100° C. for 4 hours. The NU-87 zeolite then underwent a treatment with a 7N nitric acid solution at about 100° C. for 5 hours. The volume V of the nitric acid employed (in ml) was 10 times the weight W of the dry NU87 zeolite (V/W=10). This treatment with a 7N nitric acid solution was carried out a second time under the same operating conditions At the end of these treatments, the zeolite obtained was in its H form and had an overall Si/Al atomic ratio of 33.3 and a Na content of 10 ppm.

The IM-5 zeolite was synthesized as described in Example 1 of patent application EP-A-0 946 416 or U.S. Pat. No. 6,136,290, the contents of each of those documents being hereby incorporated by reference.

TABLE 1

| 10 MR and 12 MR zeolites | | | |
|---|---|---|---|
| Zeolites | Si/Al (XRF) | Na (ppm) | Type |
| Beta | 12.5 | 87 | 12 MR |
| ZSM-5 | 17.5 | 132 | 10 MR |
| Mordenite | 10.0 | 109 | 12 MR |
| IM-5 | 12.0 | 84 | 10 MR |
| NU87 | 33.3 | 10 | 10 MR |
| Y | 15.3 | 63 | 12 MR |
| EU-1 | 18.3 | 50 | |

The zeolites, which were in the powdered state, were mechanically mixed then formed by extrusion with an alumina gel to obtain, after drying at 100° C. overnight and calcining at 500° C. in dry air, a support which contained, by weight, 15% of zeolites (each support containing an EU-1 zeolite, a 10 MR zeolite and a 12 MR zeolite) and 85% alumina. The zeolitic portion of the support was constituted by a mechanical mixture of three different zeolites, produced before forming. The weight distribution of the zeolites in the zeolitic support and the type of zeolites present in each support are given in Table 2.

To prepare catalysts C2 to C8, the zeolitic support comprising a mixture of three different zeolites, namely at least one zeolite with structure type EUO, at least one 10 MR zeolite and at least one 12 MR zeolite, underwent dry impregnation using a solution of a metallic precursor, either a solution of hexachloroplatinic acid $H_2PtCl_6$ when the metal was platinum (C2 to C5 and C8) or a solution of perrhenic acid when the metal was rhenium (C6 and C7). For catalyst C7, indium was deposited by dry impregnation with indium chloride deposited onto the support after dry impregnation of rhenium and drying at 120° C. overnight. For catalyst C8, tin was deposited by dry impregnation of tin chloride deposited onto the support after dry impregnation of Pt and drying overnight at 120° C.

After depositing all the metals on the various supports, each moist solid was then dried at 120° C. for 12 hours and calcined in a stream of dry air at a temperature of 500° C. for one hour. The composition of the catalysts obtained is shown in Table 2.

TABLE 2

Catalysts containing a EU-1 zeolite, a 10 MR zeolite, and a 12 MR zeolite

| Catalyst | Zeolite(s) | Distribution of zeolites | % metal |
|---|---|---|---|
| C1 | EU-1 + ZSM-5 + beta | 50/25/25 | None |
| C2 | EU-1 + ZSM-5 + beta | 50/25/25 | 0.3% Pt |
| C3 | EU-1 + ZSM-5 + mordenite | 50/25/25 | 0.3% Pt |
| C4 | EU-1 + IM-5 + beta | 50/25/25 | 0.3% Pt |
| C5 | EU-1 + Y + NU-87 | 50/10/40 | 0.3% Pt |
| C6 | EU-1 + ZSM-5 + mordenite | 50/10/40 | 0.3% Re |
| C7 | EU-1 + ZSM-5 + mordenite | 50/10/40 | 0.3% Re—0.3% In |
| C8 | EU-1 + ZSM-5 + mordenite | 50/25/25 | 0.3% Pt—0.3% Sn |

EXAMPLE 3

Evaluation of Catalytic Properties of Catalysts C0 to C8 by Isomerization of an Aromatic C8 Cut The performances of catalysts C0 to C8 were evaluated by isomerizing an aromatic cut comprising aromatic compounds containing eight carbon atoms per molecule, principally meta-xylene, ortho-xylene and ethylbenzene. The operating conditions employed were as follows:
temperature=390° C.;
pressure=15 bars;
partial pressure of $H_2$=12 bars.

The catalysts were pre-treated with a feed containing dimethyldisulphide (DMDS) in the presence of hydrogen, with a concentration such that the atomic ratio of sulphur to metal was 1.5. The catalysts were then kept for 3 hours at 400° C. in a stream of hydrogen and the feed was then injected.

The catalysts were compared in terms of activity by ethylbenzene conversion and in terms of selectivity by the net losses at quasi iso-equilibrium of para-xylene.

The isomerization reaction leads to side reactions generating three types of losses: losses to paraffins, essentially resulting from naphthene ring opening reactions followed by cracking, losses to aromatics formed by disproportionation and transalkylation of aromatics containing 8 carbon atoms (AC8), and finally losses to napthenes including napthenes containing 8 carbon atoms (N8) due to aromatic hydrogenation. Since the N8s can be recycled, the losses by cracking and disproportionation/transalkylation including naphthenes other than N8 (the sum of which constitutes the net losses) will be compared.

The losses by cracking (P1) are losses of AC8 in the form of paraffins (PAR) containing one to eight carbon atoms:

$P1$ (wt %)=100×[(% $PAR_{effluent}$×effluent weight)−(% $PAR_{feed}$×weight of feed)]/(% $AC8_{feed}$×wt of feed).

The losses by disproportionation/transalkylation (P2) are losses of AC8 in the form of naphthenes other than N8, of toluene, of benzene and of C9+ aromatics (OAN):

$P2$ (wt %)=100×[(% $OAN_{effluent}$×effluent weight)−(% $OAN_{feed}$×weight of feed)]/(% $AC8_{feed}$×wt of feed).

The sum of losses P1 and P2 represents the net losses.

The data shown in Table 3 were obtained at iso-experimental conditions and quasi iso-equilibrium (98%).

TABLE 3

Catalytic evaluation of catalysts C0 to C8.

| Catalyst | C0 | C1 | C2 | C3 | C4 | C5 | C6 | C7 | C8 |
|---|---|---|---|---|---|---|---|---|---|
| EB conversion (%) | 61.3 | 61.9 | 62.8 | 63.2 | 62.2 | 63.1 | 64.2 | 64.3 | 63.4 |
| Net losses (wt %) | 6.2 | 5.9 | 5.7 | 5.1 | 4.8 | 4.9 | 5.8 | 5.4 | 4.9 |

Catalysts C1 to C8 of the invention, which each comprised a zeolite with structure type EUO, a 10 MR zeolite and a 12 MR zeolite, produced better conversions of ethylbenzene and a reduction in net losses meaning that secondary reactions were limited compared with the performances obtained using a catalyst C0 which was based on only one zeolite with structure type EUO. The introduction of a metal, platinum or rhenium, onto the support (C2 to C6) also reduced the net losses and improved the ethylbenzene conversion compared with a catalyst C1 which was free of metal. The introduction of an additional metal, tin or indium (C8, C7 respectively) reduced the net losses even more significantly and further improved the ethylbenzene conversion compared with the performances obtained with a catalyst containing only a single metal (C3, C6 respectively).

The invention claimed is:

1. A composite catalyst comprising a combination of at least one zeolite with structure type EUO, at least one zeolite having channels the opening to which is defined by a ring of 10 oxygen atoms (10 MR), at least one zeolite having channels the opening to which is defined by a ring of 12 oxygen atoms (12 MR), and at least one porous mineral matrix.

2. A catalyst according to claim 1, further comprising at least one metal selected from metals from groups VIB, VIIB and VIII of the periodic table of the elements.

3. A catalyst according to claim 1, comprising at least one metal from group VIII of the periodic table of the elements.

4. A catalyst according to claim 1, in which said catalyst comprises platinum.

5. A catalyst according to claim 1, in which the zeolite with channels the opening to which is defined by a ring of 10 oxygen atoms is selected from ZSM-5, NU-87, IM-5, ferrierite, NU-85 and ZSM-22.

6. A catalyst according to claim 1, in which the zeolite with channels the opening to which is defined by a ring of 10 oxygen atoms is a ZSM-5 zeolite.

7. A catalyst according to claim 1, in which the zeolite with channels the opening to which is defined by a ring of 12 oxygen atoms is selected from beta, Y, mordenite, ZSM-12, mazzite and boggsite zeolites.

8. A catalyst according to claim 1, in which the zeolite with channels the opening to which is defined by a ring of 12 oxygen atoms is mordenite.

9. A catalyst according to claim 1, in which the zeolite with channels the opening to which is defined by a ring of 12 oxygen atoms is beta zeolite.

10. A catalyst according to claim 1, comprising an EU-1 zeolite.

11. A catalyst according to claim 1, further comprising at least one zeolite with channels the opening to which is defined by a ring of 8 oxygen atoms (8 MR).

12. A catalyst according to claim 2, further comprising at least one metal selected from metals from groups IIA and IVA of the periodic table of the elements.

13. A catalyst according to claim 1, further comprising sulphur.

14. In a process comprising catalytically isomerizing a feed comprising aromatic compounds containing eight carbon atoms per molecule, the improvement wherein the catalyst is according to claim 1.

15. An isomerization process according to claim 14, in which said feed comprises a mixture of xylenes and ethylbenzene.

16. An isomerization process according to claim 15, carried out at a temperature in the range 300° C. to 500° C., with a partial pressure of hydrogen in the range 0.3 to 1.5 MPa, with a total pressure in the range 0.45 to 1.9 MPa and an hourly space velocity, expressed in kilograms of feed introduced per kilogram of catalyst per hour, in the range 0.25 to 30 $h^{-1}$.

17. A catalyst according to claim 4, in which the zeolite with channels the opening to which is defined by a ring of 10 oxygen atoms is a ZSM-5 zeolite.

18. A catalyst according to claim 17, in which the zeolite with channels the opening to which is defined by a ring of 12 oxygen atoms is mordenite or a beta zeolite.

19. A catalyst according to claim 18, comprising an EU-1 zeolite.

20. A catalyst according to claim 19, further comprising at least one zeolite with channels the opening to which is defined by a ring of 8 oxygen atoms (8 MR).

21. A catalyst according to claim 20, further comprising at least one metal selected from metals from groups IIA and IVA of the periodic table of the elements.

22. A catalyst according to claim 21, further comprising sulphur.

23. In a process comprising catalytically isomerizing a feed comprising aromatic compounds containing eight carbon atoms per molecule, the improvement wherein the catalyst is according to claim 19.

24. An isomerization process according to claim 23, in which said feed comprises a mixture of xylenes and ethylbenzene.

25. A catalyst according to claim 1, comprising one of the following combinations:
 (C1) EU-1+ZSM-5+beta
 (C2) EU-1+ZSM-5+beta+Pt
 (C3) EU-1+ZSM-5+mordenite+Pt
 (C4) EU-1+IM-5+beta+Pt
 (C5) EU-1+Y+NU-8+Pt
 (C6) EU-1+ZSM-5+mordenite+Re
 (C7) EU-1+ZSM-5+mordenite+Re+In
 (C8) EU-1+ZSM-5+mordenite+Pt+Sn.

26. A catalyst according to claim 25, further comprising sulphur.

27. In a process comprising catalytically isomerizing a feed comprising aromatic compounds containing eight carbon atoms per molecule, the improvement wherein the catalyst is according to claim 25.

* * * * *

UNITED STATES PATENT AND TRADEMARK OFFICE
CERTIFICATE OF CORRECTION

PATENT NO. : 7,982,083 B2  
APPLICATION NO. : 12/158753  
DATED : July 19, 2011  
INVENTOR(S) : Guillon et al.

Page 1 of 1

It is certified that error appears in the above-identified patent and that said Letters Patent is hereby corrected as shown below:

Column 13, line 2 reads "least one metal selected from metals from groups IIA and IVA" should read -- least one metal selected from metals from groups IIIA and IVA --

Column 14, line 2 reads "least one metal selected from metals from groups IIA and IVA" should read -- least one metal selected from metals from groups IIIA and IVA --

Signed and Sealed this  
Fifteenth Day of November, 2011

David J. Kappos  
*Director of the United States Patent and Trademark Office*